(12) United States Patent
Cai (10) Patent No.: US 9,504,255 B2
(45) Date of Patent: Nov. 29, 2016

(54) PHYSICAL ANTIMICROBIAL METHOD (71) Applicant: NMS TECHNOLOGIES CO., LTD., Nanjing (CN)

(72) Inventor: Youliang Cai, Nanjing (CN)

(73) Assignee: NMS TECHNOLOGIES CO., LTD., Nanjing (CN)

(*) Notice: Subject to any disclaimer, the term of this patent is extended or adjusted under 35 U.S.C. 154(b) by 0 days.

(21) Appl. No.: 14/416,678

(22) PCT Filed: Jul. 16, 2013

(86) PCT No.: PCT/CN2013/079433
§ 371 (c)(1),
(2) Date: Jan. 23, 2015

(87) PCT Pub. No.: WO2014/019452
PCT Pub. Date: Feb. 6, 2014

(65) Prior Publication Data
US 2015/0173366 A1 Jun. 25, 2015

(30) Foreign Application Priority Data
Aug. 1, 2012 (CN) .......................... 2012 1 0271421

(51) Int. Cl.
*A01N 55/00* (2006.01)
*A61K 9/70* (2006.01)
*A61N 1/40* (2006.01)
*A61K 45/06* (2006.01)
*A61K 31/695* (2006.01)

(52) U.S. Cl.
CPC ............. *A01N 55/00* (2013.01); *A61K 9/7015* (2013.01); *A61K 31/695* (2013.01); *A61K 45/06* (2013.01); *A61N 1/40* (2013.01)

(58) Field of Classification Search
CPC ........... A61K 31/695; A61K 2300/00; A61K 45/06; A61K 9/7015; A01N 55/00; A01N 1/40
See application file for complete search history.

(56) References Cited

U.S. PATENT DOCUMENTS

| | | | |
|---|---|---|---|
| 4,812,263 A | 3/1989 | Login | |
| 4,898,957 A | 2/1990 | Pleueddemann et al. | |
| 5,235,082 A | 8/1993 | Hill et al. | |
| 2002/0119205 A1* | 8/2002 | Hassan | A61K 33/18 424/667 |
| 2006/0110348 A1 | 5/2006 | Ohlhausen et al. | |
| 2008/0181862 A1 | 7/2008 | Chisholm et al. | |
| 2011/0271873 A1 | 11/2011 | Ohlhausen et al. | |

FOREIGN PATENT DOCUMENTS

| | | |
|---|---|---|
| CN | 1593151 A | 3/2005 |
| CN | 1792158 A | 6/2006 |

(Continued)

OTHER PUBLICATIONS

Zhenghong Gao et al., "The Quaternization of Amino-group Silicone Oil and the Study of the Antimicrobial Effect", Journal of Soochow University (Engineering Science Edition), Apr. 30, 2007 (Apr. 30, 2007), vol. 27, No. 2, pp. 40-43, ISSN 1673-047X.

(Continued)

*Primary Examiner* — Aradhana Sasan
(74) *Attorney, Agent, or Firm* — Miles & Stockbridge P.C.

(57) ABSTRACT

The present invention relates to a physical antimicrobial method, which has the action of combating or inhibiting microorganisms when applied to the surface of human or animal body or an object. The method is safe for human body, and can prevent drug resistance caused by an antibacterial drug.

21 Claims, 1 Drawing Sheet

(56) References Cited

FOREIGN PATENT DOCUMENTS

| | | |
|---|---|---|
| CN | 101343242 A | 1/2009 |
| CN | 101972612 A | 2/2011 |
| CN | 102531928 A | 7/2012 |
| JP | H01233264 A | 9/1989 |
| JP | 2000-080064 A | 3/2000 |
| JP | 2004-137241 | 5/2004 |
| WO | 97-41876 A1 | 11/1997 |
| WO | 00-72850 A1 | 12/2000 |
| WO | 2004-087226 A1 | 10/2004 |
| WO | 2004-105687 A2 | 12/2004 |
| WO | 2006-065318 A2 | 6/2006 |
| WO | 2008-076839 A2 | 6/2008 |
| WO | 2011-020586 A2 | 2/2011 |
| WO | 2012-014762 A1 | 2/2012 |

OTHER PUBLICATIONS

Junying Li et al., "Synthesis of Polyorganosiloxane Quaternary Ammonium Salt and Its Antibiotic Property", China Surfactant Detergent & Cosmetics, Jun. 30, 2004 (Jun. 30, 2004), vol. 34, No. 3, pp. 154-156, ISSN 1001-1803.

Wentao Zhang et al., "Preparation and antibacterial properties of silicone-modified polyurethane with pendent quaternary ammonium salts", New Chemical Materials, Sep. 30, 2012 (Sep. 30, 2012), vol. 40, No. 9, pp. 116-119.

Ira Yudovin-Farber et al., "Antibacterial effect of complete resins containing quaternary ammonium polyethyleneimine nanoparticles", Journal of Nanoparticle Research; an Interdisciplinary Forum for Nanoscale Science and Technology, Kluwer Academic Publishers, Do, vol. 12, No. 2, Apr. 21, 2009, pp. 591-603.

Xia Xu et al., "Synthesis and Antimicrobial Activity of Nano-fumed Silica Derivative with N, N-dimethyl-n-hexadecylamine", Jan. 1, 2006, XA055251507, http://www.lifesciencesite.com/lsj/life0301/life-0301-11.pdf.

Supama Dugal et al., "A novel strategy to control emerging drug resistant infections", Pharm. Res., Jan. 1, 2011, XP055251514, http://jocpr.com/vol3-iss1-2011/JCPR-3-1-584-589.pdf.

Beatriz Rasines et al., "Water-stable ammonium-terminated carbosilane dendrimers as efficient antibacterial agents", Dalton Transactions: The International Journal for Inorganic, Organometallic and Bioinorganic Chemistry, Royal Society of Chemistry, GB, No. 40, Oct. 2009, pp. 8704-8713.

* cited by examiner

PHYSICAL ANTIMICROBIAL METHOD

TECHNICAL FIELD

The present invention relates to a physical antimicrobial method, particularly to antimicrobial nano-films with positive charges and physical antimicrobial methods of applying the nano-film on human body or other objects.

BACKGROUND ART

Physical antimicrobial method is a traditional method for preventing infections and spread of pathogenic microorganisms. Common physical antimicrobial methods include high temperature, high pressure and ultraviolet sterilization methods, etc. But these traditional physical antimicrobial methods are harmful when directly used in the human body, so they are essentially used to disinfect objects and spaces, unused in the human body. Generally antimicrobial methods for human body can only rely on a variety of antimicrobial agents.

At present, antimicrobial methods for use in human body are chemical and biological methods, in which antimicrobial agents exert antimicrobial action by the mechanisms selected from preventing the synthesis of bacterial cell wall, affecting the function of cell membranes, inhibiting protein synthesis, and affecting the metabolism of nucleic acids and folic acid etc. These mechanisms can achieve antimicrobial function only by antimicrobial drugs binding to pathogenic microorganisms and even entering the body thereof. The clinical use of antimicrobial drugs, especially the abuse of antimicrobial drugs results in the production of a large number of drug-resistant strains, and thus becomes an important problem to hinder clinical medical development.

In addition to traditional antimicrobial methods, there are some new antimicrobial methods at present, such as nano-silver antimicrobial and so on. In nano-silver dressing, $Ag^+$ kills pathogenic microorganisms by penetrating cell membrane. This mechanism is similar to chemical antimicrobial principle, and damages normal human cells, and may have drug resistance when used topically.

Classical microbiology is against planktonic bacteria. However, with further study on bacteria and infections, it has been found that in nature, in some industrial environment and in and outside human and animal body, majority of bacteria are attached to the surface of living or non-living objects, growing in biofilm (BF) manner not in planktonic mode. Biofilm is formed by enclosing bacteria with extracellular matrix to form special structure such as honeycomb-shape with very complex ecosystem in which bacteria can exchange information (see, for example Donlan, R. M., Biofilms and device-associated infections, Emerg. Infect. Dis, 2001.7, 277-281; C. Schaudinn, P. Stoodley, A. Kainovic, T. O'Keefe, B. Costerton, D. Robinson, M. Baum, G. Erlich, and P. Webster, Bacterial biofilms, other structures seen as mainstream concepts, Microbe, 2007 2, 231-237; and H.-C. Flemming, T. R. Neu, and D. J. Wozniak, The EPS Matrix, The "House of Biofilm Cells", J. Bacteriol, 2007; 18 (22), 7945-7947). After the formation of the biofilm, bacteria can withstand washing, phagocytosis and antimicrobial agents (see, e.g. Trautner B W, Darouiche R O, Role of biofilm in catheter-associated urinary tract infection, AM J Infect Control, 2004, 32, 177-83 and Costerton J, Geesey G, Cheng K, How bacteria stick, Sci Am, 1978, 238, 86-95).

New methods have been studied to prevent and alter the formation of biofilm, including furanone, Furacilin, silver-containing preparations, etc. (see, for example J. R. Johnson, P. Delavari, and M. Azar, Activities of a nitrofurazone-containing urinary catheter and a silver hydrogel catheter against multidrug-resistant bacteria characteristic of catheter-associated urinary tract infection, Antimicrob. Agents Chemother, 1999, 43, 2990-2995; J. R. Johnson, T. Berggren, and A. J. Conway, Activity of a nitrofurazone matrix urinary catheter against catheter-associated uropathogens, Antimicrob Agents Chemother, 1993, 37, 2033-2036; P Tenke, B Kovacs, Bjerkl and T E Johansen, et al, European and Asian guidelines on management and prevention of catheter-associated urinary tract infections, Int J Antimicrob Agents, 2008; Vol. 31, Suppl 1, pp S68-78; and Kunin C M, Nosocomial urinary tract infections and the indwelling catheter: what is new and what is true? Chest. 2001, 120, 10-12). However, these methods also have some drawbacks.

Thus, it is still desirable to provide novel antimicrobial methods and relevant preparations capable of avoiding drug resistance.

BRIEF DESCRIPTION OF ART

Figure 2:
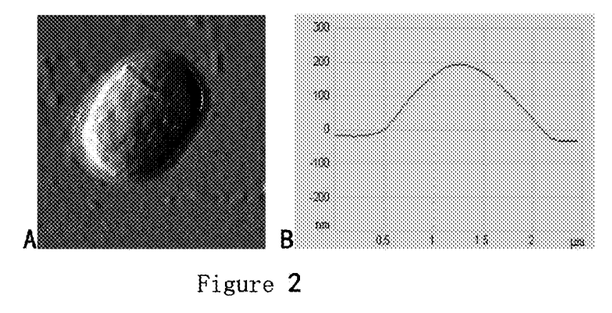
Figure 3:
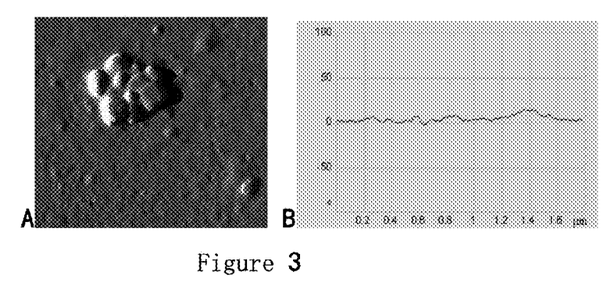

An objective of the present invention is to provide a physical antimicrobial method to solve the problem of drug-resistant strains caused by antibacterial drugs by physical methods and to solve the problem that classic antibacterial methods have no prevention and treatment action to bacterial biofilm. The antimicrobial mechanism of the present invention is to rupture *E. coli* cell membrane by physical effect of static electricity of charges to thereby inactivate the pathogen. The mechanism is shown in FIGS. 2 and 3.

Figure 1:
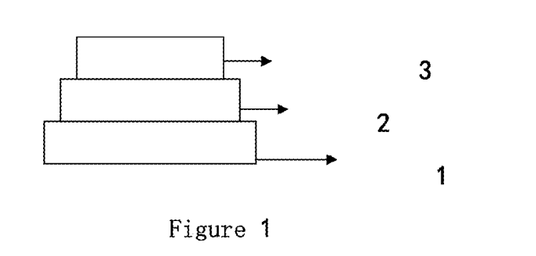
FIG. 1: shows a schematic diagram of physical antimicrobial film in an embodiment of the present invention.

An objective of the present invention is to provide an antimicrobial nano-film on the surface of human or animal body or an object. The structure of the film is shown in FIG. 1.

Another objective of the present invention is to provide an organosilicone diquaternary ammonium salt of formula (I):

$$(R^1R^2R^3N^+X^-)\!\!-\!\!R^5\!\!-\!\!(R^1R^2R^3N^+X^-) \qquad (I)$$

wherein, $R^1$ is independently a $C_{8-18}$ alkyl group, a $C_{8-18}$ alkenyl group or a $C_{8-18}$ alkynyl group, preferably a $C_{8-18}$ linear alkyl group; $R^2$ and $R^3$ are independently methyl or ethyl; $R^5$ is $C_{3-10}$ alkylene, which is substituted in β-site or farther site by tri ($C_{1-3}$ alkoxy) silyloxy or tri ($C_{1-3}$ alkoxy) silyl-$C_{1-6}$ alkoxy; and $X^-$ is independently a pharmaceutically acceptable counter anion, preferably $Cl^-$ or $Br^-$.

Another objective of the present invention is to provide a physical antimicrobial method, the method comprising applying said organosilicone diquaternary ammonium salt of formula (I) on the surface of objects in need of antimicrobial treatment.

Physical antimicrobial method can avoid the drug resistance problem which chemical and biological antimicrobial methods encounter.

Another objective of the invention is to provide an antimicrobial composition comprising said organosilicone diquaternary ammonium salt of formula (I) and at least one excipient. The antimicrobial composition of the present invention forms a nano-film with quaternary cation at the site in need of antimicrobial treatment after being applied. The nano-film can effectively kill pathogenic microorganisms, and can effectively prevent the formation of bacterial biofilms and/or damage the bacterial biofilms which have been formed to overcome the limitations that classical antibacterial methods are generally only effective against planktonic bacteria but not effective against bacterial biofilms.

BRIEF DESCRIPTION OF DRAWINGS

A and B in FIG. 2 are atomic force microscope graphs of untreated *Escherichia coli*.

A and B in FIG. 3 are atomic force microscope graphs of *Escherichia coli* treated with the antimicrobial compositions of the present invention.

DETAILED DESCRIPTION OF THE PREFERRED EMBODIMENTS OF THE INVENTION

In the first aspect, the antimicrobial methods and products of the present invention are mainly used for the prevention and treatment of a variety of topical infections in human body and nosocomial infections.

In one embodiment, clinical experiments prove that the antimicrobial composition of the present invention is equivalent in therapeutic efficacy to typical antimicrobial drugs in the treatment of local infections, and can be used for treating bacterial infections, fungal infections, viral infections, and other pathogenic infections.

In one embodiment, the treatment solution of topical infections of the present invention includes the treatment of the infections of bacteria (e.g. *Staphylococcus aureus, Escherichia coli, Pseudomonas aeruginosa, Neisseria gonorrhoeae*) and clinical diseases caused by these bacterial infections (e.g. impetigo, bacterial balanoposthitis etc.); infections of fungi (e.g. *Candida albicans, Trichophyton rubrum, Epidermophyton floccosum*, etc.) and clinical disease caused by these fungal infections (such as *Candida albicans* vaginitis, athlete's foot, etc.); infections of viruses (human papilloma virus, varicella zoster virus, human immunodeficiency virus) and clinical diseases caused by these viral infections (such as condyloma *acuminatum*, herpes zoster, AIDS, etc.), and infections of other pathogens (such as *Treponema pallidum, mycoplasma, chlamydia*, etc.) and clinical diseases caused by these pathogenic infections (e.g. mycoplasmal urethritis, chlamydial urethritis, syphilis, etc.). Embodiments of the present invention demonstrate that the antimicrobial composition of the present invention exhibits remarkable effect in the treatment of impetigo, *Candida albicans* vaginitis, herpes zoster and condyloma *acuminatum* and the prevention of recurrence thereof.

In one embodiment, the prevention and treatment of the nosocomial infections related in the present invention is achieved by preventing bacterial biofilm formation and strengthening hand hygiene to reduce the incidence of nosocomial infections, shorten hospital stay, and reduce hospital costs. In one embodiment, the nosocomial infections are reduced by reducing infections associated with medical catheter and cannula, surgical incision infections and infections associated with artificial implant materials, and by strengthening hand hygiene.

In one embodiment, the examples of said infections associated with medical catheter and cannula include, but are not limited to infections associated with urethral catheter, tracheal cannula, peritoneal dialysis tubes, venous cannula, fistula catheter, and interventional catheter.

In one embodiment, the surgical incisions can be a variety of surgical incisions, such as oral surgical incisions, gastrointestinal surgical incisions, perineal incisions, anorectal surgical incisions, cosmetic surgery incisions, etc.

In one embodiment, the examples of said artificial implant materials include, but are not limited to, bone screws, artificial joints and artificial valves.

In one embodiment, the improvement of hand hygiene includes applying the antimicrobial composition of the present invention to the hands of medical personnel to maintain the hands sterile for at least one hour, or at least 2 hours, or at least 4 hours, or at least 8 hours in order to reduce the bacteria spread by medical staff due to check and operation, thereby reducing the incidence of nosocomial infections.

In one embodiment, the methods and products of the invention are also useful for the prevention of pathogenic microbial infections so as to prolong allowable time of wound infections. The application of the antimicrobial compositions of the present invention in early stage of trauma can win valuable time for medical evacuation and late debridement and reduce disability and death occurring late due to infections.

In one embodiment, the methods and products of the present invention can be used for the prevention and treatment of the infections of a variety of acute and chronic wounds.

In one embodiment, the examples of said acute wounds include, but are not limited to cuts, lacerations, abrasions and other open wounds and burns. The antimicrobial composition of the present invention can be conveniently used in sites in human body which are not easily or cannot be treated by conventional dressings, can accelerate wound healing and prevent secondary infections.

In one embodiment, the examples of chronic wounds include, but are not limited to pressure ulcers, diabetic foot ulcer, and venous leg ulcers. Delayed healing of chronic wounds is related to biofilms formed on the surface of wound. The antimicrobial composition of the present invention can prevent the formation of bacterial biofilms and destruct the bacterial biofilms formed, and accelerate wound healing.

In one embodiment, the antimicrobial compositions of the present invention also has the effect of inhibiting colonization of tumor cells, can be used for the prevention and treatment of various types of tumors (e.g., squamous cell carcinoma, liposarcoma, adenocarcinoma etc.), and various neoplastic diseases (such as oral cancer, bladder cancer, pelvic cancer, head and neck cancer, etc.). The examples of the present invention demonstrate that in animal models, the physical antimicrobial membranes formed with the antimicrobial composition of the present invention have the action of inhibiting tumor cell growth.

In one embodiment, the antimicrobial compositions of the invention are also useful for clinical testing for fluid discharges and secretions of artificial cavity and natural cavity in human body, wherein the antimicrobial composition of the present invention is used to exclude false-positive microorganism interference. In a preferred embodiment, the antimicrobial composition of the present invention is used to improve a method for detecting prostate fluid, wherein the physical antimicrobial film of the present invention is used for distinguishing the source of leukocyte in prostate fluid and improving the accuracy of the prostatic fluid examination.

In the second aspect, the present invention provides an organosilicone diquaternary ammonium salt of formula (I):

$$(R^1R^2N^+X^-)-R^5-(R^1R^2R^3N^+X^-) \qquad (I)$$

wherein, $R^1$ is independently a $C_{8-18}$ alkyl group, a $C_{8-18}$ alkenyl group or a $C_{8-18}$ alkynyl group, preferably a $C_{8-18}$ linear alkyl group; $R^2$ and $R^3$ are independently methyl or ethyl; $R^5$ is $C_{3-10}$ alkylene, which is substituted in β-site or farther site by tri ($C_{1-3}$ alkoxy) silyloxy or tri ($C_{1-3}$ alkoxy) silyl-$C_{1-6}$ alkoxy; and $X^-$ is independently a pharmaceutically acceptable counter anion, preferably $Cl^-$ or $Br^-$.

In the present invention, the term "β-site or farther site" refers to the site of one or more carbon atoms distanced from the carbon atoms (referred to as α-position) attached to the quaternary group.

In one embodiment, in the formula (I) $R^5$ is a group of the formula: —$(CH_2)_n CH(OR_6Si(OCH_2CH_3)_3)(CH_2)_n$— wherein 1≤n≤3; $R^6$ is a single bond or a $C_{1-3}$ alkylene group.

The organosilicone diquaternary ammonium salt of formula (I) may be used for the formation of antimicrobial membrane on the surface of an object in need of antimicrobial treatment, such as on the skin of human. Cytotoxicity experiments, sensitization test, skin and mucous membrane irritation test prove that the organosilicone diquaternary ammonium salts of formula (I) have no toxic side effects, and exhibit safe antimicrobial effect.

In the third aspect, the present invention provides an antimicrobial method, which comprises applying the silicone diquaternary ammonium salt of formula (I) on the surface of the object in need of antimicrobial treatment:

$$(R^1R^2R^3N^+X^-) - R^5 - (R^1R^2R^3N^+X^-) \quad (I)$$

wherein, $R^1$ is independently a $C_{8-18}$ alkyl group, a $C_{8-18}$ alkenyl group or a $C_{8-18}$ alkynyl group, preferably a $C_{8-18}$ linear alkyl group; $R^2$ and $R^3$ are independently methyl or ethyl; $R^5$ is $C_{3-10}$ alkylene, which is substituted in β-site or farther site by tri ($C_{1-3}$ alkoxy) silyloxy or tri ($C_{1-3}$ alkoxy) silyl-$C_{1-6}$ alkoxy; and $X^-$ is independently a pharmaceutically acceptable counter anion, preferably $Cl^-$ or $Br^-$.

In one embodiment, in the formula (I) $R^5$ is a group of the formula: —$(CH_2)_n CH(OR_6Si(OCH_2CH_3)_3)(CH_2)_n$— wherein 1≤n≤3; $R^6$ is a single bond or a $C_{1-3}$ alkylene group.

After the organosilicone diquaternary ammonium salt of formula (I) is applied to the surface of an object in need of antimicrobial treatment, especially on the human skin, the quaternary ammonium salt group provides a potential of +40 mv~+80 mv on the surface.

It is known that in the range of pH 6.0~8.0, for example, under the conditions of about pH 7.0, the zeta potential of pathogenic microorganisms is generally in the range of −50~0 mv, and the zeta potential of the most pathogenic microorganisms is in the range of −40~0 mv. For example, the zeta potential of *actinobacillus* actinomycetem comitans and *Klebsiella* is about −50~−40 mv, the zeta potential of *Penicillium* oxalate is −15~−10 mv, the zeta potential of *Aspergillus terreus* is less than −20 mv; the zeta potential of *Beauveria bassiana* is −30~0 mv; the zeta potential of mycelium of *Penicillium chrysogenum* is −20~−10 mv; the zeta potential of spores of *Aspergillus fumigatus* is −20.2±1.6 mv, and the zeta potential of adenovirus, MS2, Norwalk, Qβ, HIV is in the range of −25~0 mv.

It is also known that the potential of cell membrane of the human body is −80~−100 mv.

In the present invention, the polysilicone diquaternay ammonium salts with average particle size of nanoscale (1 nm-1000 nm) are formed by polymerization of organosilicone diquaternay ammonium salt of formula (I) by a "bottom-up" nano-process. The nanoscale polysilicone diquaternary ammonium salt has +40 mv+80 mv potential, and can kill pathogenic microorganism target, without causing damage of normal human cells. Moreover, the nanoscale polysilicone diquaternary ammonium salt does not penetrate the cell membrane, using static electricity to sterilize, rather than relying on binding to pathogenic microorganisms or entering the body thereof to complete antimicrobial functions, and thus will not develop drug resistance. Further, the antimicrobial film formed in the antimicrobial method may prevent the formation of bacterial biofilms, which provides an innovative and effective method for the prevention and treatment local infections and nosocomial infections associated with biofilms.

In one embodiment, the antimicrobial method of the present invention comprises applying the organosilicone diquaternary ammonium salt of formula (I) on the surface of an object in need of antimicrobial treatment to form antimicrobial film with quaternary ammonium cation. The antimicrobial film is composed of the polymer particles of the organosilicone diquaternary ammonium salt of formula (I). Preferably, the average particle diameter of the polymer particles constituting the antimicrobial membrane with quaternary ammonium cation is in the range of 1 nm~1000 nm.

In one embodiment, the potential of the antimicrobial membrane with quaternary ammonium cation is in the range of +40~+80 mv.

In one embodiment, the antimicrobial method of the present invention can kill a variety of negatively charged pathogenic microorganisms, including bacteria, fungi, viruses, such as *Staphylococcus aureus, Pseudomonas aeruginosa, Candida albicans, Escherichia coli*, SARS coronavirus, hepatitis B virus, human papilloma virus, human immunodeficiency virus (HIV), *Treponema pallidum*, etc.

In one embodiment, the microbicidal mode used in the antimicrobial method of the invention is physical mode through electrostatic force to rupture the cell membranes of pathogenic microorganisms or cause morphological changes so as to cause death of pathogenic microorganisms, rather than chemical or biological mode commonly used in conventional antimicrobial drugs.

In another embodiment, the physical antimicrobial method of the invention does not result in the development of drug-resistant strains.

In another embodiment, the nanoscale polymer formed with organosilicone diquaternary ammonium salt of formula (I) is not absorbed by human cells and does not enter human body to metabolism, and is safe in cytotoxicity experiments, sensitization test, skin irritation test, acute oral toxicity test in mice, acute dermal irritation test in rabbits, multiple (chronic) skin irritation test in rabbits, eye irritation test in rabbits, and micronucleus test in cells.

In one embodiment, the antimicrobial method of the present invention is an antimicrobial method in human body, wherein the organosilicone diquaternary ammonium salt of formula (I) is applied to the surface of human body.

In another embodiment, the antimicrobial method of the present invention is an antimicrobial method in an object, wherein the organosilicone diquaternary ammonium salt of formula (I) is applied to the surface of an object in need of antimicrobial treatment, such as the surface of medical device.

In the fourth aspect, the present invention provides an antimicrobial composition comprising the organosilicone diquaternary ammonium salt of formula (I) according to the present invention and at least one excipient.

In one embodiment, as shown in FIG. 1, 3 is a functional film having various functions of healing, anti-itch, pain relieving, anti-inflammation, hemostasis, anti-adhesion, anti-tumor, scar-removing, etc. The films are bonded to or overlaid with the antimicrobial films, and can be composed of materials having various functions, such as healing-promoting materials, anti-itch materials, pain relieving materials, anti-inflammatory materials, hemostatic materials, anti-adhesion materials, anti-tumor materials, scar-removing materials.

In one embodiment, the content of the organosilicone diquaternary ammonium salt in the antimicrobial composition is 0.1-30 wt. %, based on the total weight of the composition.

In one embodiment, the excipient is selected from the group consisting of water and liquid organic solvents, such as alcohols, ethers, ketones and esters.

In one embodiment, the antimicrobial composition further comprises at least one excipient, e.g., fragrances, flavoring agents, surfactants, emulsifiers, antioxidants, stabilizers, thickening agents, aerosol propellants, and combinations thereof.

In one embodiment, the antimicrobial composition is in the form of a spray, lotion, granule, liniment, varnish, ointment, coating formulation, and the form which can be used to soak an object.

In one embodiment, the antimicrobial composition or the organosilicone quaternary ammonium salt may be combined with other materials or devices to form a composite device. Examples of the other materials or devices include, but are not limited to chitosan, fibrin glue, gelatin and collagen, collagen protein, sodium hyaluronate, icodextrin, liquid glue, Lactated Ringer's solution, cellulose regenerated by oxidization, expanded PTFE, translucent membrane dressings, hydrocolloid dressings, alginate dressings, anti-allergic gel, Zenieva, seprafilm, hyskon, silica gel, wound adhesives, dental adhesives, bone cement, and nano-silver. If desired, these materials or devices may be used in combination of two or more.

In one embodiment, the antimicrobial composition may further comprise at least one additional active ingredient to form a composition having composite functions. The examples of the active ingredients include, but are not limited to oxymatrine, chitosan, Dencichine, Bletilla mannan, Bufalin, ginsenosides, *Impatiens pritzellii* saponins, Evodiamine, Asiaticoside, Shikonin, catechin, emodin, allantoin, molting ketones, salvianic acid, Daphnetin, ferulic acid, quercetin glycosides, curcumin, baicalin, paeonol, pestle lemon aldehyde, cinnamic aldehyde, eugenol, berberine, menthol, Osthol, quercetin, glycyrrhizin, Rhein, Astragaloside A, resveratrol, Wogonin, berbamine, sophoridine, Cinobufagin, and Proanthocyanidins.

In one embodiment, the antimicrobial composition is in the form of hydrogel, comprising organosilicone diquaternary ammonium salt of formula (I), water, and one or more of polyethylene oxide, polyvinyl alcohol, polyvinyl pyrrolidone, polyalginate, sodium polyacrylate, and chitosan. In one embodiment, the viscosity of the antimicrobial composition in hydrogel form makes it suitable for filling wounds. In another embodiment, the viscosity of the antimicrobial composition in hydrogel form makes it suitable as ointment.

In one embodiment, the antimicrobial composition is in the form of ointment.

In one embodiment, the antimicrobial composition is in the form of aqueous gel, which comprises an organosilicone diquaternary ammonium salt of formula (I), water, and aqueous polymer, such as sodium carboxymethyl cellulose, gelatin, agar, or combinations thereof.

In one embodiment, the antimicrobial composition of the present invention in the form of aqueous gel or hydrogel is further coated on a substrate, such as a transparent or translucent or opaque film or foam thin sheet. Optionally, at least part of the substrate is coated with adhesive, so as to adhere to, e.g. human skin.

In one embodiment, the antimicrobial composition of the present invention in the form of aqueous gel or hydrogel according to the present invention is further coated on a carrier or adsorbed into the carrier so as to obtain a fixed shape, wherein the carrier is e.g. paper, cloth (e.g., flannel, woven fabric, non-woven fabric), synthetic resins (e.g., polyurethane, ethylene/vinyl acetate copolymer, polyvinyl chloride, polyester (e.g., polyethylene terephthalate), polyolefins (e.g., polyethylene, polypropylene), polyamides (such as nylon 6, nylon 66), polyvinylidene chloride, polytetrafluoroethylene), rubber, or a cellulose derivative.

It is general knowledge in the art to formulate the organosilicone diquaternary ammonium salt of formula (I) into a suitable antimicrobial composition dosage form according to intended use.

In one embodiment, the antimicrobial composition of the present invention is sprayed onto the skin to form an antimicrobial film, which can remain antimicrobial effect in 8 hours.

In one embodiment, the antimicrobial composition of the present invention is sprayed on the surface of fabric, which can still remain antimicrobial effect after being washed with detergent for 40 times.

In the fifth aspect, the present invention provides a product having an antimicrobial function, such as medical device.

An article having antimicrobial function can be formed by applying the antimicrobial composition of the present invention to the surface of the article, such as medical device.

In one embodiment, the antimicrobial composition of the present invention can be applied to the surface of a variety of medical devices for antibacterial effect, and can be combined with these medical devices to form medical devices with antimicrobial functions. Examples of the medical devices include medical basic surgical instruments, microsurgical instruments, neurosurgical instruments, ophthalmic surgical instruments, otorhinolaryngological surgical instruments, dental surgical instruments, thoracic cardiovascular surgical instruments, abdominal surgical instruments, urinary and anorectal surgical instruments, plastic surgery (orthopedic) surgical instruments, gynecological surgical instruments, surgical instruments for Planned Parenthood, puncture and injection instrument, surgical instruments for burns department (plastic surgery), general examination equipment, medical electronic equipment, medical optical equipment, instruments and endoscopic equipment, medical laser equipment, high-frequency medical equipment, physical therapy equipment, equipment for traditional Chinese medicine, medical supplies and equipment for radiation protection, medical laboratory equipment and basic instruments, equipment for extracorporeal circulation and blood processing, implant materials and artificial organs, equipment and appliances for operating room and consulting room, dental equipment and apparatus, ward care equipment and appliances, medical equipment and appliances for cryotherapy and refrigeration, dental materials, medical materials and dressings, medical suture materials and adhesives, medical polymer materials and products, interventional equipment and so on.

In the sixth aspect, the present invention provides products having the function of antimicrobe, deodorization such as materials having the function of antimicrobe, deodorization. Objects having the function of antimicrobe, being mildewproof and deodorization can be formed by applying the antimicrobial composition of the present invention to the surface of articles such as materials of antimicrobe and deodorization.

In one embodiment, the antimicrobial compositions of the present invention can be used in combination with other materials having the function of antimicrobe and deodorization to form various combined materials, which can be widely used in antimicrobe, mildewproof and deodorization treatment of various industries. These combined materials can be combined with the articles in these industries to form new combination objects. These industries include agriculture, forestry, animal husbandry and fishery, construction and building materials, metallurgy and mining, petrochemistry, transportation, information industry, mechanical and electrical machinery, garments and textile, environmental protection and afforestation, tourism and leisure, office supplies, toys, gifts, antiques, household items, paper industry, sporting goods, office furniture, and so on.

Embodiments

Following embodiments are given to better illustrate the present invention, not to limit the scope of the present invention.

Embodiment 1

Schematic Diagram of Physical Antimicrobial Films

FIG. 1 shows a schematic diagram of the physical antimicrobial film according to one embodiment of the present invention. In FIG. 1, 1 is a body surface, which may be the skin (including mucous membranes) or a variety of other objects; 2 is a physical antimicrobial film, which has positive charges and is adhered or adsorbed to the surface of body surface 1; 3 is an optionally other functional film.

It should be understood that although the physical antimicrobial film is shown as a planar structure, it may also be a variety of curved surface structures.

Embodiment 2

Preparation of Organosilicone Diquaternary Ammonium Salt

Embodiment 2a

Preparation of Organosilicone Diquaternary Ammonium Salt 1

Organosilicone diquaternary ammonium salt 1, wherein R, R' are $C_{12}H_{25}$, $X^-$ is $Cl^-$.

(1) Synthesis of double long-chain alkyl quaternary ammonium salt having a hydroxyl-containing linking group.

To a three-necked flask were added 0.2 mol of dodecyl dimethyl amine and 40 ml of isopropanol-water mixed solvent (isopropyl alcohol and water in a volume ratio of 10:1). The mixtures were heated with stirring to 50° C., and then thereto was added dropwise 0.21 mol of epichlorohydrin and allowed to react for 3 hours to obtain epoxypropyl dodecyl dimethyl ammonium chloride.

0.2 mol of additional dodecyl dimethyl amine was added slowly to the reaction mixture obtained in above reaction step, and 10% hydrochloric acid was added dropwise to maintain the reaction mixture to pH 9. After the addition was completed, the reaction mixture was heated to 70° C. and allowed to react for 5 hours. After the solvent and residual reactants were removed under reduced pressure, a pale yellow waxy solid was obtained, i.e., diquaternary ammonium salt having a hydroxyl-containing linking group: 2-hydroxy-1,3-bisdodecyl dimethyl ammonium propane dichloride. In this reaction, the conversion rate of amine was more than 95%. The diquaternary ammonium salt having a hydroxyl-containing linking group was dried at 50° C. for 10 hours in a vacuum oven for standby use.

(2) Synthesis of Organosilicone Diquaternary Ammonium Salt 1

0.1 mol of 2-hydroxy-1,3-bisdodecyl dimethyl ammonium propane dichloride and 100 ml of isopropanol were added to a round bottom flask, to which was slowly added 0.1 mol of ethyl orthosilicate. The mixtures were heated to 45° C. with stirring under reflux conditions. It was observed that the solid was gradually dissolved, and the resulting solution was muddy white. After the reaction was carried out for 12 hours, the resultant was distilled under reduced pressure to remove the residual reactants, and then dried in a vacuum oven at 50° C. for 10 hours, a white waxy solid, i.e., an organosilicone diquaternary ammonium salt 1: 2-triethoxy silyloxy-1,3-didodecyl dimethyl ammonium propane dichloride was obtained.

IR (cm$^{-1}$): 3411, 2924, 2854, 1636, 1468, 1097, 799. $^1$H NMR (300 MHz, DCCl$_3$): δ (ppm): 0.79, t, CH$_3$(CH$_2$)$_{11}$ 6H; 1.05-1.08, t, (CH$_3$CH$_2$O)$_3$Si, 1.11-1.20, m, CH$_3$(CH$_2$)$_9$CH$_2$CH$_2$N 45H; 1.64, m, CH$_3$(CH$_2$)$_9$CH$_2$CH$_2$N 4H; 3.02, m, CH$_3$(CH$_2$)$_9$CH$_2$CH$_2$N 4H; 3.23, d, (CH$_2$)$_2$N(CH$_3$)$_2$ 12H; 3.54, t, CH$_3$(CH$_2$)$_9$CH$_2$CH$_2$N(CH$_3$)$_2$CH$_2$CHO 4H; 3.66, m, (CH$_3$CH$_2$O)$_3$Si 6H; 4.70, m, (NCH$_2$)$_2$CHO 1H.

Embodiment 2b

Synthesis of Organosilicone Diquaternary Ammonium Salt 2

Organosilicone Diquaternary Ammonium Salt 2, wherein R, R' are $C_{12}H_{25}$, $X^-$ is $Cl^-$ 0.1 mol of 2-hydroxy-1,3-bisdodecyl dimethyl ammonium propane dichloride and 100 ml of isopropanol were added to a round bottom flask, to which was slowly added 0.1 mol of α-chloropropyltriethoxysilane. The mixtures were heated to 45° C. with stirring under reflux conditions. It was observed that the solid was gradually dissolved, and the resulting solution was muddy white. After the reaction was carried out for 12 hours, the resultant was distilled under reduced pressure to remove the residual reactants, and then dried in a vacuum oven at 50° C. for 10 hours, a white waxy solid, i.e., an organosilicone diquaternary ammonium salt 2: 2-triethoxy silicopropoxy-1,3-didodecyl dimethyl ammonium propane dichloride was obtained, 95% yield.

$^1$H NMR (300 MHz, DCCl$_3$): δ (ppm): 0.90, t, CH$_3$(CH$_2$)$_{11}$ 6H; 1.22-1.24 t, (CH$_3$CH$_2$O)$_3$SiCH$_2$CH$_2$CH$_2$O, 1.25-1.37, m, CH$_3$(CH$_2$)$_9$CH$_2$CH$_2$N 45H; 1.87-1.90, m, CH$_3$(CH$_2$)$_9$CH$_2$CH$_2$N 4H; 3.40, m, CH$_3$(CH$_2$)$_9$CH$_2$CH$_2$N 4H; 3.43-3.70, m, CH$_3$(CH$_2$)$_9$CH$_2$CH$_2$NCH$_2$(CH$_3$)$_2$ 28H; 5.19, m, (—NCH$_2$)$_2$CH—O—CH$_2$— 1H.

Embodiment 3
Preparation of 2% Physicalantimicrobial Composition 2 parts by weight of organosilicone diquaternary ammonium salt prepared in Embodiment 2 and 98 aliquots of deionized water were mixed and emulsified to prepare a 2% physical antimicrobial composition.

Embodiment 4
Determination of the Particle Size and Potential of the Physical Antimicrobial Composition The 2% physical antimicrobial compositions prepared in Embodiment 3 was diluted with deionized water to an aqueous solution having 0.5 wt. % of the organosilicone diquaternary ammonium salt. The particle size of the polymer in the antimicrobial composition and the change of the potential as pH value were measured by using Brookhaven ZetaPlus particle size analyzer and Brookhaven 90Plus system. The measurement results showed that the antimicrobial composition had a relatively high cationic charge potential, the charge potential was in the range between +50 mV and +60 mV in the measured pH range (3-12). The average particle size of a single particle was 2.57 nm, and the mean diameter of aggregate was 43.5 nm.

Embodiment 5
Sterilization Mechanism Experiments of Physical Antimicrobial Composition The physical antimicrobial composition solution prepared in Embodiment 3 was diluted to the minimum bactericidal concentration of 188 pm, and then used for treating *E. coli*. The morphological change of the *E. coli* cell membrane before and after the treatment was observed by atomic force microscopy.

In FIG. 2, A is morphological photograph of a single *E. coli* untreated. In FIG. 3, A is morphological photograph of a single *E. coli* treated by destruction. FIG. 2-A showed that the structure of the *E. coli* cell membrane untreated was complete, and there was no gap or pits on the surface of cell; FIG. 2-B was scanning pattern of a cross-section, showing that the complete cell membrane height was about 200 nm; FIG. 2-B and FIG. 2-A together showed that the cell membrane of *E. coli* was oval. FIG. 3-A displayed that the structure of *E. coli* cell membrane was completely destroyed after treatment; scanning pattern 3B showed that the cell membrane which was damaged or collapsed cell membrane was of zigzag shape, with a height of less than 20 nm, which further proved that the membrane morphology had been destroyed; FIG. 3-B and FIG. 3-A together showed that the destroyed *E. coli* cell membrane was of irregular shape. Accordingly, the antimicrobial mechanism of the antimicrobial composition according to the present invention was to destroy the *E. coli* cell membrane by physical action of charge electrostatic force so as to inactivate pathogens.

Embodiment 6
Killing Effect of the Physical Antimicrobial Composition on Various Planktonic Pathogenic Microorganisms The solution prepared in Embodiment 3 was diluted in different proportions, and its activity of killing various pathogenic microorganisms in the suspension was measured by the method described in European BS EN 1040: 2005 (for bacteria), BS EN 1275: 2005 (for fungi), and BS EN 14476: 2005 (for virus). The results showed that the antimicrobial solution exhibited killing effect on various pathogenic microorganisms, as shown in following table.

| Type of pathogenic microorganisms | Dilution proportion | Killing rate |
|---|---|---|
| Escherichia coli | 1:100 | 99.95% |
| Staphylococcus aureus | 1:50 | 99.94% |
| Pseudomonas aeruginosa | 1:32 | 99.90% |
| Candida albicans | 1:5 | 99.95% |
| SARS coronavirus | 1:80 | 100% |
| Natural germs on hands | stock solution | 91.52% |
| Hepatitis B virus | stock solution | having destroying action |
| Treponema pallidum | 1:20 | having immobilization action |
| Neisseria gonorrhoeae | 1:320 | having inactivation action |

Embodiment 7
Killing Effect of the Physical Antimicrobial Composition on the Bacteria on the Surface of Various Materials According to the method regulated in European BS EN13697:2001, in the temperature range between 18° C.±1° C. and 25° C.±1° C., various test surface samples were aseptically placed in petri dish, then 0.05 ml of each bacterial suspension was placed on each test surface, and 0.1 ml of the physical antimicrobial composition and hard water were placed on each test surface, after contacting with the bacteria for 5 minutes and in contact with fungi for 15 minutes, the Ig value of each test surface colony forming unit was counted. The results showed that the physical antimicrobial composition exhibited antibacterial activity when applied to following various surfaces.

| Surface | Result | | | | | | | | |
|---|---|---|---|---|---|---|---|---|---|
| | Acinetobacter baumannii (lg) | Aspergillus niger (lg) | Candida albicans (lg) | Clostridium difficile (lg) | Escherichia coli (lg) | Enterococcus hirae (lg) | MRSA (lg) | Pseudomonas aeruginosa (lg) | Staphylococcus aureus (lg) |
| Stainless steel | | | | 3.7 | | | | | |
| Wood floor | >6.1 | 2.9 | 2.6 | 2.6 | 3.8 | 4.1 | 3.8 | 4.6 | 3.9 |
| plexi glass | >6.1 | >5.7 | 3.2 | 2.6 | 3.6 | 4.1 | 3.9 | 4.2 | 4.1 |
| Plastic rotary handle | >6.1 | 3.7 | 2.2 | 2.2 | 3.7 | 3.9 | 3.7 | 3.4 | 4.2 |
| Terylener Nylon Safety band | >6.1 | >5.7 | 3.2 | 3.7 | 4.2 | 4.3 | 3.8 | 2.9 | 4.7 |

| Surface | Acinetobacter baumannii (lg) | Aspergillus niger (lg) | Candida albicans (lg) | Clostridium difficile (lg) | Escherichia coli (lg) | Enterococcus hirae (lg) | MRSA (lg) | Pseudomonas aeruginosa (lg) | Staphylococcus aureus (lg) |
|---|---|---|---|---|---|---|---|---|---|
| Steel | 3.2 | 5.3 | 2.8 | 1.9 | 3.5 | 3.9 | 4.1 | 4.6 | 4.3 |
| Aluminum alloy Stretcher | 3.4 | 3.8 | 3.3 | 3.7 | 4.2 | 5.1 | 3.7 | 2.9 | 3.9 |

Embodiment 8

Drug-Resistance Experiment

The experiment was carried out according to U.S. NCCLS 1997 standard. More than 300 pathogens isolated from the Department of Burns were taken to conduct drug-resistance test with commonly used antibiotics and the solution prepared in Embodiment 3. The isolated pathogens included seven species, i.e. *Escherichia coli, Staphylococcus aureus, Pseudomonas aeruginosa, Acinetobacter, Klebsiella pneumoniae, Enterobacter aerogenes*, and *Enterobacter cloacae*, which are commonly used in clinic. The resistance rate of *Escherichia coli* to ampicillin, gentamicin and cefazolin was 80.1%, 40.9%, and 40.0% respectively; resistance rate of MSSA to penicillin was 87.0%; resistance rate of *Pseudomonas aeruginosa* to piperazine amoxicillin, gentamicin and ceftazidime was 34.1%, 35.3% and 21.7% respectively; resistance rate of *Acinetobacter* to piperacillin, gentamicin and ceftazidime was 93.3%, 18.9% and 21.2% respectively; resistance rate of *aerogenes* to gentamicin and cefazolin was 8.2% and 79.3% respectively, resistance rate of *Enterobacter cloacae* to gentamicin and cefazolin was 28.1% and 89.3% respectively. These isolated bacteria are all sensitive to the physical antimicrobial composition of the present invention, i.e. resistance rate was 0. This showed that the physical antimicrobial composition of the invention has broad spectrum antimicrobial characteristics.

Embodiment 9

Toxic Side-Effect Experiments

The solution prepared in Example 3 was subjected to biological safety according to the method described according to ISO10993. The results showed that the physical antimicrobial composition of the present invention was very safe, had no toxic side effect. Sensitization test, skin irritation test and cytotoxicity experiments were all qualified.

| Experimental name | Standard | Results |
|---|---|---|
| Cytotoxicity experiment | <level 3 | Level 2 |
| Sensitization test | Should meet requirements | Meeting requirements |
| Skin irritation test | Should have no skin irritation response | Meeting requirements |
| Mouse acute oral toxicity test | LD50 value of more than 10000 mg/kg b.wt | At non-toxic level |
| Rabbit acute skin irritation test | Skin irritation index of 10.8 | Without irritation |
| Rabbit multiple (chronic) skin irritation test | Skin irritation index of 10.8, average pathogenic score of 1.5 | Belonging to no irritation |
| Rabbit eye irritation test | Rabbit acute eye irritation score index (maximum) of 3.5, and average eye irritation index of 0 in 48 hours | Belonging to no irritation |
| Cell micronucleus test | Negative | Meeting requirements |

Embodiment 10

Experiment of Prevention of Biofilm Growth

Sterile siliconized latex urethral catheter was cut into 16 sample fragments, and then the sample fragments were randomly divided into experimental group and control group, which were soaked respectively in the solution prepared in Embodiment 3 and distilled water for 5 minutes. The sample fragments were placed in a culture medium containing *E. coli* and cultured at 37° C. The sample fragments were made into samples for observing under the scanning electron microscope and confocal laser scanning microscope respectively. Scanning electron microscopy showed that the experimental group fragment had no *E. coli* adhesion in 7 days, with no biofilm formation being found; while the control group fragment had a large amount of *E. coli* adhesion and biofilm structure was formed. Confocal laser scanning microscopy showed that transparent antimicrobial film was observed on the surface of the experimental group fragments, with a thickness of 40 to 41.5 nm.

Embodiment 11

Long-Lasting Antimicrobial Experiment

The solution prepared in Embodiment 3 was subjected to antibacterial experiments on the surface of the skin and fabric. The method was as follows:

Embodiment 11a

Antibacterial Experiment on Skin Surface

According to the experimental method of European BS EN 1499: 1997, the finger was immersed in a solution containing *E. coli*, and then the finger was sprayed with the solution prepared in Embodiment 3. The bacterial inhibition rate was observed. The results showed that the antibacterial rate in 8 hours was 99.95%.

Embodiment 11 b

Antibacterial Experiments on Fabric Surface

In accordance with the method of European BS EN 1040: 2005, at 20° C.±1° C. the cotton cloth sprayed with the solution prepared in Embodiment 3 was washed with a detergent for 5 minutes and then dried, as once washing. The results after washing for 40 times showed that the antibacterial rate was 99.97%.

Embodiment 12

This embodiment provides different dosage forms of the antimicrobial compositions of the present invention and preparation methods thereof.

Embodiment 12a

A spray was prepared according to the following formulation:

| Name of API | Proportion |
| --- | --- |
| Organosilicone diqunternary ammonium salt | 2 wt. % |
| Flavors | 1 wt. ‰ |
| Chitosan | 4 wt. % |
| Water | 939 wt. ‰ |

The organosilicone diquaternary ammonium salt prepared in Embodiment 2 was added to purified water to emulsify, added with chitosan and flavors, and mixed to prepare an aqueous formulation, which was dispensed into HDPE bottle mounted with a nozzle.

Embodiment 12b

A spray was prepared according to the following formulation:

| Name of raw material | proportion |
| --- | --- |
| Organosilicone diqunternary ammonium salt | 2 wt. % |
| Flavors | 1 wt. ‰ |
| Matrine | 3 wt. % |
| Water | 976 wt. ‰ |

The organosilicone diquaternary ammonium salt prepared in Embodiment 2 was added to purified water to emulsify, added matrine and flavors, and mixed to prepare an aqueous formulation, which was dispensed into HDPE bottle mounted with a nozzle.

Embodiment 13

The following experiments showed significant effect of the antimicrobial composition of the present invention.

The antimicrobial composition used in the following experiments was prepared according to the method described in Embodiment 3.

Embodiment 13a

Experiment of Treatment of Impetigo 1652 patients clinically diagnosed with impetigo by the Department of Dermatology in the hospital were chosen and randomly divided into experimental group (n=1032) and control group (n=620). The experimental group was treated with the antimicrobial composition of the invention to the affected area, and the control group was treated with mupirocin, 2 times a day, for 7 days. The results showed that the experimental and control group had an effective rate of 90.5% and 85% respectively, and there was no significantly statistical difference between two groups. The experiments showed that the antimicrobial composition of the present invention had same effect as mupirocin in the treatment of impetigo, but without dressing, easy to use.

Embodiment 13b

Treatment of Vulvovaginal Candidiasis (VVC)

In this experiment, 100 patients clinically diagnosed with clinical VVC were chosen and randomly divided into experimental group (n=50) and control group (n=50). The experimental group was sprayed with the antimicrobial composition to vulva every day in addition to routine topical application of vaginal suppository, econazole nitrate, 3 times a day. The control group was applied with Mupirocin Ointment and Bifonazole Ointment to vulva in addition to routine topical application of vaginal suppository, econazole nitrate each day. The results showed that in seven days, the experimental and control group had a total effective rate of 98% and 97% respectively, without significant difference between them. The results showed that the antimicrobial composition of the present invention had the same therapeutic effect as the combination of antifungal drug and antibacterial drug in the treatment of VVC. Moreover, the physical antimicrobial method for human body can eliminate the source of infections and prevent ascending infections and VVC recurrence when used in underwear and sanitary napkin.

Embodiment 13c

Experiment of Treatment of Herpes Zoster 113 elderly patients with herpes zoster were divided into two groups, treatment group (n=57) and control group (n=56). The treatment group was administered orally with Acyclovir Tablets at 200 mg, 5 times a day, and topically applied with the antimicrobial composition for the lesion site, three times a day; the control group was administered orally with Acyclovir Tablets at 200 mg, 5 times a day, and topically applied with Calamine Lotion; and the course of treatment was two weeks in both groups. The total effective rate in treatment group (the ratio of the patient with pain relief and skin lesions subsided within two weeks of medication) was 97%, while the total effective rate in the control group was 87%, without statistical significance between them. The treatment group exhibited significantly shorter blistering time, pain-relieving time, crusting time and recovery time than the control group. The experiment showed that the antimicrobial composition of the invention in combination with antiviral agent had better effect than antiviral agent alone.

Embodiment 13d

Clinical Experiment of Treatment and Prevention of Recurrence of Condyloma Acuminatum In this experiment, 242 patients with condyloma acuminatum were chosen and randomly divided into experimental group (n=121) and control group (n=121). The experimental group underwent $CO_2$ laser surgery and then applied topically with the above antimicrobial compositions, including underwear and other contact sites, twice a day, continuously for 3 months. The control group underwent surgery and then applied topically with erythromycin ointment, twice a day continuously for 3 months. The results showed that the recurrence rate of the experimental and control group was 18.07% and 51.8% respectively; and there was no significant difference between the two groups. This experiment demonstrated that the antimicrobial compositions of the present invention can assist chemotherapy or surgery, and significantly reduce the recurrence rate of condyloma acuminatum.

Embodiment 13e

Experiment of Preventing Catheter Associated Urinary Tract Infection (CAUTI)

In this experiment, patients underwent catheterization after clinical urological surgery were chosen and randomly divided into experimental group (n=310) and control group (n=310). The control group was routinely applied with normal saline, twice a day. The experimental group was sprayed with the antimicrobial composition described above, twice a day, in addition to routine application of normal saline. The experimental results showed that the occurrence rates of CAUTI were significantly different between two groups on the fifth and seventh day. The infection rate of the control group was 16.7% on the fifth day and 23.3% on the seventh day. The infection rate of the experimental group was 3.3% on the fifth and seventh day. This experiment confirmed that the use of the antimicrobial compositions of the invention for indwelling urethral catheter care can effectively reduce the chance of urinary tract infection.

Embodiment 13f
Experiment of Prevention of Ventilator-Associated Pneumonia (VAP)

In this experiment, 325 patients applied with ventilator were divided into experimental group (n=166) and control group (n=159). The experimental group was subjected to brushing with routine oral mouthwash and then applied with the antimicrobial composition, 3 times a day; the control group was subjected to oral and nasal care with normal saline, 3 times a day. VAP occurred in 8.5% of the patients in experimental group; and VAP occurred in 53.3% of the patients in control group. The results of the two groups exhibited significant difference, $P<0.01$. This experiment confirmed that the use of antimicrobial compositions of the invention for oral and nasal care can effectively reduce the colonization of pathogens in the mouth, nose, and throat to thereby reduce and delay the incidence of VAP.

Embodiment 13g
Experiment of Preventing Perineal Incision Infection 164 puerperas underwent vaginal delivery and perineal incision were chosen, 82 of which in control group received routine care, i.e., disinfecting perineal incision and surrounding tissue with 0.5% iodophor cotton ball, twice daily, and 82 of which in observation group received routine care and treatment with the antimicrobial composition thereof. By comparing the pain degree of puerpera incision, the observation group was better than the control group ($P<0.05$); and by comparing the healing of puerperal perineal incision, the observation group was better than the control group ($P<0.05$). This experiment confirmed that the antimicrobial composition of the invention has the functions of long-lasting antimicrobe, pain relief, isolation of wound surface and promotion of wound healing in perineal incision.

Embodiment 13h

Experiment of preventing pin tract infection after external skeletal fixation 80 patients with external skeletal fixation of lower extremity were randomly divided into two groups; in the treatment groups the stitch hole of the patients was sterilized with 75% alcohol cotton ball, and the stitch hole was treated with the antimicrobial composition, and finally dressed with 75% alcohol "Y" shaped opening yarn, once a day; in the control group the stitch hole of the patients was sterilized with 75% alcohol cotton ball, and then dressed with 75% alcohol "Y" shaped opening yarn, once a day.

The bacterial culture of the treatment group was negative, while the positive rate of the control group was 13.5%. The treatment group exhibited significantly lower infection symptom and pain extent than those of the control group. This experiment showed that the antimicrobial composition of the present invention exhibited significant effect in prevention of pin tract infection after lower extremity fracture external fixation.

Embodiment 13i
Improvement of Hand Hygiene

The bacteria on the hands of medical staff were sampled for testing. The bacteria were monitored at different time periods i.e. before and 8 hours after applying the antimicrobial composition, and the data were statistically analyzed. A total of 16 persons were monitored for 96 times in two months. The number of the bacteria was significantly less after application than before application with a qualified rate of 97.5%. This experiment demonstrated that the antimicrobial compositions of the present invention can prevent the hand skin of clinical staff from carrying pathogens.

Embodiment 13j
Prevention of Gonococcal Infection

The vagina of female BALB/c mice was inoculated with *Neisseria gonorrhoeae* WHO-L. The mouse vagina in the experimental group was protected with the antimicrobial film formed with the antimicrobial composition; the mouse vagina in the control group was treated with deionized water. At 2-10 days after inoculation, the proportion of average number of PMNs to total number of cells in the stained smear of mouse vaginal secretion was monitored; at 2, 4 and 5 days after inoculation, vaginal secretions were taken for culture of *Neisseria gonorrhoeae*; dissemination of *Neisseria gonorrhoeae* from females to males was simulated: the sexual intercourse was simulated on the females infected with *Neisseria gonorrhoeae*, with the mouse penis replaced by a glass rod. The glass rod of the experimental group was soaked with the antimicrobial composition while the glass rod of the control group was soaked with deionized water. The secretions on the glass rod tip were eluted for gonococcal culture to compare the detection rate. In the experiment of simulating dissemination of *Neisseria gonorrhoeae* from males to females, the percentage of PMNs in the experimental group mice at 5-8 days after inoculation was significantly lower than that in the control group ($P<0.05$). The experimental group exhibited lower positive rate of gonococcal culture than the control group ($P<0.01$). In the experiment of simulating dissemination of *Neisseria gonorrhoeae* from females to males, the positive rate of gonococcal culture in the experimental group of mice was significantly lower than that in the control group ($P<0.01$). This showed that the physical antimicrobial molecular film formed can prevent the infection or colonization of *Neisseria gonorrhoeae* in the productive tract of female mice, and can play the role of liquid condom for male mice.

Embodiment 13k
Experiment of Delaying Infection Occurrence Time

In this experiment, rabbit models in burns in combination with artificial infection with *Pseudomonas aeruginosa* were employed. The experimental and control groups were treated in the affected areas respectively with the antimicrobial composition and water solvent. At 1, 2, 4, 7 and 14 days before and after experiments, rabbit serum was collected, body temperature was measured, and inflammatory factor levels such as WBC counts, serum $NO_2^-/NO_3^-$ levels, serum TNF levels, and serum superoxide anion, and indexes of liver and kidney functions such as alanine aminotransferase, alkaline phosphatase, aspartic acid transferase, creatinine and urea nitrogen were detected. The experimental results showed that pharmacodynamic detection indicators were elevated in a slower rate in the experimental group than in the control group, and finally the two groups reached higher infection indicators. The results showed that the antimicrobial composition of the present invention can effectively delay the occurrence of wound infection when applied in early stage of wound.

Embodiment 13l
Treatment of Open Wounds 250 patients with open wounds, such as abrasions, falls, and cuts, were chosen and randomly divided into experimental and control groups, 125 each. The experimental group was subjected to routine wound debridement and cleaning and then treated with the antimicrobial compositions plus a sterile gauze dressing twice a day until the pink granulation tissue was present in the wound, and finally treated with dressing once a day until healed. The control group was subjected to routine wound debridement and cleaning, and covered with sterile gauze, with dressing time and treatment course same as described in the experimental group. The results showed that the total effective rate of the experimental group was 100% while the total effective rate of the control group was 86%, and the two groups exhibited very significant difference. This experiment demonstrated that administration of the antimicrobial compositions of the present invention in the treatment of open wounds can improve effective rate, accelerate wound healing, and reduce the medical expenses for the patients.

Embodiment 13m

Treatment of Burns

In this experiment, 370 burn patients were chosen and randomly divided into the experimental group (n=195) and the control group (n=175). The experimental group was treated with Bromogeramine for debridement and then applied externally with the antimicrobial composition, three times a day; the control group was treated with Bromogeramine for debridement, and applied externally with silver sulfadiazine ointment, three times a day. The results showed there was no significant difference in positive bacterial detection rate on wound, wound edge response and healing time (P>0.05), but the experiment group was obviously better than the control group in pain tolerance (P<0.05). This experiment demonstrated that the antimicrobial composition of the present invention had comprehensive therapeutic effect of on burns equivalent to SSD, but exhibited significant effect in pain relief and good compliance.

Embodiment 13n

Treatment of Pressure Ulcers

In this experiment, 163 patients clinically diagnosed with stage II and stage III pressure ulcers were randomly divided into the experimental group (n=82) and the control group (n=81). The control group was treated using routine care methods, i.e. disinfecting the skin around the wound, cleaning the wound and removing necrotic tissues and foreign bodies, disinfecting again and covering with sterile gauze and cotton pad; daily dressing changes was determined upon exudation. In addition to above nursing care and dressing change as employed in the control group, the experimental group was further sprayed with the antimicrobial composition. The clinical results were shown below. This experiment demonstrated that the antimicrobial compositions of the present invention was capable of destroying and preventing the formation of biofilms and converting non-healing wounds to healing wounds so as to accelerate wound healing.

Wound Healing of Pressure Ulcer Experiment

| Methods | Number of cases | Healing rate | Effective rate | Healing time of stage II pressure ulcers | Healing time of stage III pressure ulcers |
|---|---|---|---|---|---|
| Experimental group | 82 | 86.90% | 93.30% | 6.97 ± 1.2 | 10.0 ± 1.5 |
| Control group | 81 | 27.00% | 76.50% | 11.12 ± 1.8 | 18.0 ± 2.3 |
| P value | | <0.05 | <0.01 | <0.05 | <0.05 |

Embodiment 13o

Inhibition of Tumor Transplantation

In the experiment, 40 male Wistar rats were randomly divided into the control group and the experimental group. The liver cancer cell stains of R15 rats were used to prepare animal tumor models. The experimental group was protected by using the antimicrobial composition and compared with the control group. The results showed that the incidence of tumors in the control group was approximately 66.7%, and the incidence of tumors in the experimental group was approximately 29.4%. The experimental group and control group were significantly statistically different (p<0.05) in tumor incidence, and had no difference in tumor formation during pathomorphological examination.

Embodiment 13p

Improved Detection of Prostatic Fluid

The antimicrobial composition was injected into the urethra in human body, and after 5 minutes, the prostate fluid was detected. The antimicrobial composition can adsorb negatively charged bacteria to exclude the interference of bacteria in prostatic fluid examination. In such a way, the accuracy of prostate fluid examination could be improved.

Embodiment 14

Combination with Medical Devices

The physical antimicrobial film can also be combined with medical devices to form medical devices having antimicrobial effect, as shown in the following table:

| No. | Classification of medical devices | Name of medical device |
|---|---|---|
| 1 | Basic surgical instruments | Medical suture needle, basic surgical knife, scissors, pliers, etc. |
| 2 | Microsurgical instruments | Microsurgical knife, scissors, pliers, etc. |
| 3 | Neurosurgical instruments | Neurosurgical knife for brain surgery, pliers, tweezers, etc. |
| 4 | Ophthalmic surgical instruments | Ophthalmic surgical scissors, pliers, tweezers, etc. |
| 5 | Otorhinolaryngological surgical instruments | Otorhinolaryngological knife, scissors, pliers, etc. |
| 6 | Dental surgical instruments | Dental knife, scissors, pliers, etc. |
| 7 | Thoracic and cardiovascular surgical instruments | Thoracic and cardiovascular knife, scissors, pliers, etc. |
| 8 | Abdominal surgical instruments | Abdominal surgical scissors, pliers, hooks, etc. |
| 9 | Urinary and anorectal surgical instruments | Urinary and anorectal scissors, pliers, hooks, etc. |
| 10 | Plastic (orthopedic) surgical instruments | Plastic (Orthopaedic) knife, scissors, pliers, active devices, fixtures etc. |
| 11 | Gynecological surgical instruments | Gynecological knife, scissors, pliers, etc. |
| 12 | Surgical instruments for planned parenthood | Pliers, uterine curette, oviduct extracting plates, etc. for planned parenthood |
| 13 | Puncture and injection instrument | Disposable sterile syringe, puncture needle, venous catheter, etc. |
| 14 | Surgical instruments for burns department (plastic surgery) | knife, pliers, tweezers, etc for burns deparment (plastic surgery), etc. |
| 15 | General examination equipment | thermometers, sphygmomanometers, stethoscopes, etc. |
| 16 | Medical electronic equipment | Pacemaker, implantable medical sensors, ECG diagnostic instruments, EEG diagnostic instruments, etc. |
| 17 | Medical optical equipment | IOL (intraocular lens), endoscope for cardiovascular and endovascular surgeries, ophthalmic optical instruments, etc. |
| 18 | Instrument and endoscopic equipment | Laser surgery and treatment equipment, laser surgical instruments, interventional laser treatment instrument, etc. |
| 19 | Medical laser equipment | High frequency surgical and electrocoagulation devices, microwave therapy equipment, radio frequency therapy equipment, etc. |
| 20 | Physical therapy equipment | Electrotherapy equipment, physiotherapy, biofeedback instrument, etc. |

-continued

| No. | Classification of medical devices | Name of medical device |
|---|---|---|
| 21 | Equipment for traditional Chinese medicine | Acupuncture needles, scrapping plates, electronic acupoint treatment instrument, etc. |
| 22 | Medical supplies and equipment for radiation protection | Radiation protection clothing, protective skirt, protective gloves, protective chairs, etc |
| 23 | Medical laboratory equipment and basic instruments | Vacuum blood collection tube, blood collection needles, medical incubators, etc. |
| 24 | Equipment for extracorporeal circulation and blood processing | Blood filters, water filters, hemodialysis devices, human blood processor, dialysis machine, dialysis tubes, etc. |
| 25 | Implantation materials and artificial organs | Implanted devices such as bone plates and bone nails, implantable artificial organs such as artificial joints and heart, etc, vascular stents, artificial skin, etc. |
| 26 | Equipment and appliances in operating room and consulting room | Ventilator, anesthesia machine, gastric lavage machine, auxiliary infusion devices, etc. |
| 27 | Dental equipment and apparatus | Dental driller and accessories, supragingival scaler, dental filling equipment, dental aspirator, etc. |
| 28 | Ward care equipment and apparatus | Medical air purification systems, anti-bedsore mattress, etc. |
| 29 | Medical equipment and appliances for cryotherapy and refrigeration | Cryotherapy machine, ice bag, ice caps, etc. |
| 30 | Dental materials | Polymer denture materials, dental implant materials, dental fillers, dentures, etc. |
| 31 | Medical hygienic materials and dressings | Hemostatic sponge, medical absorbent cotton, medical absorbent gauze, medical cotton balls, cotton swabs, bandages, operating coats, surgical caps, surgical pads, surgical drapes, protective clothing, protective mask, etc. |
| 32 | Medical suture materials and adhesives | Sutures, bone cements, epidermal adhesives, dental adhesives, etc. |
| 33 | Medical polymer materials and products | infusion apparatus, blood transfusion apparatus, intravenous (blood) injector, vaginal dilator, anesthesia catheters, urethral catheter, various drainage tubes, suction tube, tracheal cannula, intestinal cannula, etc. |
| 34 | Intervention equipment | central venous catheters, etc. intravascular catheters, guidewires and sheaths, embolism devices, etc. |

Embodiment 15

Combination with an Object

The physical antimicrobial membrane of the present invention can be widely used for antimicrobe, being mildewproof and deodorization in various industries, and can be combined with articles in these industries to form new combined articles, as shown in the following table:

| No. | Industry | Materials and Articles |
|---|---|---|
| 1 | Agriculture, forestry, animal husbandry and fishery | Poultry, livestock, silk, fur, flowers and trees, etc. |
| 2 | Construction and building materials | Woods and boards, stones and granites, glass, ceramics, plastic materials, metal building materials, pipe fittings, paint, etc. |
| 3 | Metallurgy and mining | Iron alloy and products thereof, steel and products thereof, magnetic materials, and other non-metallic mineral products, etc. |

-continued

| No. | Industry | Materials and Articles |
|---|---|---|
| 4 | Petrochemistry | Petroleum and petrochemical products, inorganic chemicals, organic chemicals, resins and other polymers, chemical fiber, food additives, feed additives, plastics and products thereof, rubber and products thereof, glass and products thereof, laboratory supplies, etc. |
| 5 | Transportation | Automobiles, trains, trams, ships, aircrafts, subways and contents therein, motorcycles, and bicycles, etc. |
| 6 | Information industry | A variety of computers and peripheral equipments, magnetic cards, dialers, chargers, telephones, cell phones, exchangers, fax machines, beepers, interphones, and network communication products, etc. |
| 7 | Mechanical and electrical machinery | Mechanical fan, ventilation equipment, heat exchangers, refrigeration and air conditioning equipment, instrumentations, etc. |
| 8 | Garments and textiles | Apparel, socks, shoes and shoe materials, underwear, pajamas, work clothes, uniforms, cotton fabrics, linen fabrics, silk fabrics, wool fabrics, synthetic fabrics, blended fabrics, carpets, towels, bath towels, bedding, etc. |
| 9 | Environmental protection and afforestation | Water and sewage treatment facilities, waste disposal facilities, etc. |
| 10 | Tourism and leisure | Hotels supplies, pokers, chesses, musical instruments, fitness and recreation facilities, etc. |
| 11 | Office and stationery | Books, stationery, calculators, office paper, laboratory supplies, fax machines, copiers, attendance machine, etc. |
| 12 | Toys and gifts | Wooden toys, plastic toys, stuffed toys, electronic toys, electric toys, stroller and accessories, key chain, etc. |
| 13 | Antiques | Unearthed relics, calligraphy and paintings, murals, sculptures, antiques and collectibles, etc. |
| 14 | Household items | Household appliances, home computers, home air conditioners, central air conditioning ducts, home TV, water purifiers, water dispensers, soybean milk machines, dishwashers, disinfecting cabinets, range hoods, refrigerators, humidity regulators, air purifiers, vacuum cleaners, exhaust fans, remote controllers, cutlery, cookware, kitchen facilities, sanitary facilities, sanitary ware, baby supplies, pet hair and supplies, doorbell, etc. |
| 15 | Paper industry | Automotive filter paper, toilet paper, facial tissue, napkins, disposable diapers, sanitary napkins, wet wipes, paper tableware, paper cups, paper pulp, etc. |
| 16 | Sporting supplies | Sports instrument, rehabilitation equipment, etc. |
| 17 | Office furniture | Office furniture, laboratory furniture, desks, chairs, sofas, etc. |

The invention claimed is:

1. An antimicrobial method, which is safe for human body, and does not result in the development of drug-resistance strain, the method comprising:
   applying an antimicrobial film or particle with positive charges to a surface of human or animal body or an object in need of antimicrobial treatment, wherein the thickness of the antimicrobial film or the diameter of the particles is in the range between 1 nm and 1000 nm, and the potential is in the range between +40 mV and +80 mV, and the potential ruptures a morphology of a cell membrane of microorganisms so as to achieve physical antimicrobial method, rather than chemical or biological mode, by utilization of a difference between a potential of cell membrane of microorganisms and a potential of cell membrane of the human body, said method further including applying an organosilicone diquaternary ammonium salt of formula (I) to the surface of human or animal body or an object in need of antimicrobial treatment, $$(R^1R^2R^3N^+X^-)-R^5-(R^1R^2R^3N^+X^-) \quad (I)$$

wherein, $R^1$ each is independently a $C_{6-16}$ alkyl group, a $C_{8-18}$ alkenyl group or a $C_{8-18}$ alkynyl group; $R^2$ and $R^3$ each are independently methyl or ethyl; $R^5$ is $C_{3-10}$ alkylene, which is substituted in β-site or farther site by tri ($C_{1-3}$ alkoxy) silyloxy or tri ($C_{1-3}$ alkoxy) silyl-$C_{1-6}$ alkoxy; and $X^-$ each is independently a pharmaceutically acceptable counter anion to form the antimicrobial film or particle with quaternary cation, the antimicrobial film being composed of polymer particles of the organosilicone diquaternary ammonium salt of formula (I).

2. The antimicrobial method of claim 1, wherein the antimicrobial film or particle is applied to the surface of human or animal body or an object to achieve at least one of:
killing or inhibiting microorganisms, including bacteria, fungi, viruses and other pathogens;
deodorizing or being mildewproof; or
preventing the formation of bacterial biofilms.

3. The antimicrobial method of claim 2, wherein the bacteria are selected from Acinetobacter, Staphylococcus aureus, Escherichia coli, Pseudomonas aeruginosa, Neisseria gonorrhoeae, Klebsiella pneumoniae, Enterobacter aerogenes, or Enterobacter cloacae; the fungi are selected from Candida albicans, Trichophyton rubrum, or Epidermophyton floccosum; the viruses are selected from the SARS coronavirus, hepatitis B virus, human papilloma virus, varicella zoster virus, or human immunodeficiency virus; the other pathogens are selected from Treponema pallidum, mycoplasma, or chlamydia.

4. The antimicrobial method of claim 1, the method further comprising:
applying an antimicrobial composition including the organosilicone diquaternary ammonium salt of formula (I) and at least one excipient to the surface of said human or animal body or the object in need of antimicrobial treatment.

5. The antimicrobial method of claim 1, wherein the organosilicone diquaternary ammonium salt has at least one of:
each $R^1$ is independently a $C_{8-18}$ straight chain alkyl group; or
each $X^-$ is independently $Cl^-$ or $Br^-$; and
$R^5$ is a group of the formula:
$(CH_2)_nCH(OR_6Si(OCH_2CH_3)_3)$ $(CH_2)_n$— wherein 1≤n≤3; $R^6$ is a single bond or a $C_{1-3}$ alkylene group.

6. The antimicrobial method of claim 4, wherein the antimicrobial composition has at least one of:
the composition has 0.1-30 wt% of an organosilicone diquaternary ammonium salt, based on the total weight of the composition;
the excipient includes water and liquid organic solvents;
the antimicrobial composition further comprises at least one adjuvant; or
the antimicrobial composition is in the form of a spray, lotion, granule, liniment, varnish, ointment, coating formulation, and the form which can be used to soak an object;

the antimicrobial composition further comprises at least one additional active ingredient to form a composition having combined functions; the active ingredient being various functional films having healing, relieving itching, pain relieving, anti-inflammation, hemostasis, anti-adhesion, anti-tumor, removing-scar functions.

7. An organosilicone diquaternary ammonium salt of formula (I):

$$(R^1R^2R^3N^+X^-)-R^5-(R^1R^2R^3N^+X^-) \quad (I)$$

wherein, $R^1$ each is independently a $C_{8-18}$ alkyl group, a $C_{8-18}$ alkenyl group or a $C_{8-18}$ alkynyl group; $R^2$ and $R^3$ each are independently methyl or ethyl; $R^5$ is $C_{3-10}$ alkylene, which is substituted in β-site or farther site by tri ($C_{1-3}$ alkoxy) silyloxy or tri ($C_{1-3}$ alkoxy) silyl-$C_{1-6}$ alkoxy; and $X^-$ each is independently a pharmaceutically acceptable counter anion; and
at least one excipient.

8. The organosilicone diquaternary ammonium salt according to claim 7, which has at least one of:
each $R^1$ is independently a $C_{8-18}$ straight chain alkyl group; or
each $X_-$ is independently $Cl^-$ or $Br^-$; and
$R^5$ is a group of the formula below:
$(CH_2)_nCH(OR_6Si(OCH_2CH_3)_3)$ $(CH_2)_n$— wherein 1≤n≤3; $R^6$ is a single bond or a $C_{1-3}$ alkylene group.

9. An antimicrobial composition, comprising: the organosilicone diquaternary ammonium salt of formula (I) according to claim 7; and
at least one excipient.

10. The antimcrobial composition of claim 9, further comprising at least one of:
the composition has 0.1-30 wt% of an organoscone diquaternary ammonium salt, based on the total weight of the composition;
the excipient includes water and liquid organic solvents;
the antimicrobial composition further comprises at least one adjuvant; or
the antimicrobial composition is in the form of a spray, lotion, granule, liniment varnish, ointment, coating formulation, and the form which can be used to soak an object;
the antimicrobial composition further comprises at least one additional active ingredient to form a composition having combined functions; the active ingredient being various functional films having healing, relieving itching, pain relieving, anti-inflammation, hemostasis, anti-adhesion, anti-tumor, scar-removing functions.

11. The antimicrobial composition of claim 10, wherein:
the liquid organic solvents include alcohols, ethers, ketones and esters;
the at least one adjuvant includes perfumes, flavoring agents, surfactants, emulsifiers, antioxidants, stabilizers, thickeners, aerosol propellants, and combinations thereof; or
the other active ingredients include quaternary ammonium salts, oxymatrine, chitosan, Dencichine, Bletilla mannan, Bufalin ginsenosides, Impatiens pritzelii saponins, Evodiamine, Asiaticoside, Shikonin, catechin, emodin, allantoin, ecdysterone, salvianic acid, Daphrietin ferulic acid, quercitroside, curcumin, baicalin, paeonol, citral, cinnamic aldehyde, eugenol, berberine, menthol, Osthol, quercetin, glycyrrhizin, Rhein, Astragaloside A, resveratrol, Wogonin, berbamine, sophoridine, Cinobufagin, Proanthocyanidins, and combinations thereof.

12. The antimicrobial composition according to claim 9, wherein the composition is present in one of following forms:
- a hydrogel, comprising an organosilicone diquaternary ammonium salt of formula (I), water, and one or more of polyethylene oxide, polyvinyl alcohol, polyvinyl pyrrolidone, polyalginate, sodium polyacrylate and chitosan;
- an ointment; or
- an aqueous gel, comprising an organosilicone diquaternary ammonium salt of formula (I), water, and water-soluble polymers, such as sodium carboxymethyl cellulose, gelatin, agar, or combinations thereof.

13. The antimicrobial composition of claim 12, wherein the antimicrobial composition in the form of aqueous gel or hydrogel is further coated on a substrate, or the antimicrobial composition in the form of aqueous gel or hydrogel is further coated on a carrier or absorbed in the carrier to obtain a fixed shape.

14. A combination device, comprising:
- the antimicrobial composition according to claim 9; and
- one or more materials or devices selected from the group consisting of chitosan, fibrin glue, gelatin and collagen, collagen protein, sodium hyaluronate, icodaxtrin, liquid glue, Lactated Ringer's solution, cellulose regenerated by oxidization, expanded Teflon, translucent membrane dressings, hydrocolloid dressings, alginate dressings, anti-allergic gel, Zenieva, seprafilm, hyskon, silica gel, wound adhesives, dental adhesive, bone cement, and nano-silver.

15. The antimicrobial composition of claim 9, wherein the organosilicone diquaternary ammonium salt or the antimicrobial composition including the organosilicone diquaternary ammonium salt, is applied to the surface of human or animal body or the object to achieve at least one of:
- killing or inhibiting microorganisms, including bacteria, fungi, viruses and other pathogens;
- deodorizing or being mildewproof; or
- preventing the formation of bacterial biofilms.

16. The antimicrobial composition of claim 15, wherein the bacteria are selected from Acinetobacter, Staphylococcus aureus, Escherichia coli, Pseudomonas aeruginosa, Neisseria gonorrhoeae, Klebsiella pneumoniae, Enterobacter aerogenes, or Enterobacter cloacae; the fungi are selected from Candida albicans, Trichophyton rubrum, or Epidermophyton floccosurn, the viruses are selected from the SARS-CoV virus, hepatitis B virus, human papilloma virus, varicella zoster virus, or human immunodeficiency virus; the other pathogens are selected from Treponema pallidum, mycoplasma, or chlamydia.

17. The method according to claim 1, wherein the object is a medical device selected from the group consisting of medical basic surgical instruments, microsurgical instruments, neurosurgical instruments, ophthalmic surgical instruments, otorhinolaryngological surgical instruments, dental surgical instruments, thoracic cardiovascular surgical instruments, abdominal surgical instruments, urinary and anorectal surgical instruments, plastic surgery (orthopedic) surgical instruments, gynecological surgical instruments, surgical instruments for Planned Parenthood, puncture and injection instrument, surgical instruments for burns department (plastic surgery), general examination equipment, medical electronic equipment, medical optical equipment, instruments and endoscopic equipment, medical laser equipment, high-frequency medical equipment, physical therapy equipment, equipment for traditional Chinese medicine, medical supplies and equipment for radiation protection, medical laboratory equipment and basic instruments, equipment for extracorporeal circulation and blood processing, implant materials and artificial organs, equipment and appliances for operating room and consulting room, dental equipment and apparatus, ward care equipment and apparatus, medical equipment and appliances for cryotherapy and refrigeration, dental materials, medical materials and dressings, medical suture materials and adhesives, medical polymer materials and products, and interventional equipment.

18. The method of claim 1, wherein the object includes products having the function of antimicrobe, deodorization such as materials having the function of antimicrobe, deodorization; these combined materials can also be combined with industrial products to form new combined objects; these industries includes agriculture, forestry, animal husbandry and fishery, construction and building materials, metallurgy and mining, petrochemistry, transportation, information industry, mechanical and electrical machinery, garments and textile, environmental protection and afforestation, tourism and leisure, office supplies, toys, gifts, antiques, household items, paper industry, sporting goods, or office furniture.

19. A method for achieving at least one of the following functions:
- for the prevention and treatment of a variety of topical infections in human and nosocomial infections, and prevention and treatment of the infections of various acute and chronic wounds;
- inhibiting tumor cell colonization, and clinical testing for drainage fluid and secretions of artificial cavity and natural cavity in human body:
- the method includes applying the organosilicone diquaternary ammonium salt or the antimicrobial composition of claim 9 to patients in need of achieving at least one of the above said functions.

20. The method of claim 19, wherein the topical infections in human body include bacterial infections, fungal infections, viral infections, and other pathogenic infections.

21. The method of claim 19, wherein the nosocomial infections include infections associated with medical catheter and cannula, surgical incision infections, artificial implants associated infections, and improvement of hand hygiene methods.

* * * * *